United States Patent
Mollard

(10) Patent No.: US 9,567,279 B2
(45) Date of Patent: Feb. 14, 2017

(54) METHODS FOR OXIDATION OF ALPHA TOCOTRIENOL IN THE PRESENCE OF NON-ALPHA TOCOTRIENOLS

(71) Applicant: Edison Pharmaceuticals, Inc., Mountain View, CA (US)

(72) Inventor: Paul Mollard, Saratoga, CA (US)

(73) Assignee: Edison Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 14/850,855

(22) Filed: Sep. 10, 2015

(65) Prior Publication Data

US 2016/0002138 A1 Jan. 7, 2016

Related U.S. Application Data

(63) Continuation of application No. 14/233,734, filed as application No. PCT/US2012/047455 on Jul. 19, 2012, now Pat. No. 9,162,957.

(60) Provisional application No. 61/572,645, filed on Jul. 19, 2011.

(51) Int. Cl.
| | |
|---|---|
| *C07C 46/00* | (2006.01) |
| *C07C 403/00* | (2006.01) |
| *C07D 311/00* | (2006.01) |
| *C07C 46/06* | (2006.01) |
| *C07D 311/72* | (2006.01) |
| *C07C 403/08* | (2006.01) |

(52) U.S. Cl.
CPC ............. *C07C 46/06* (2013.01); *C07C 403/08* (2013.01); *C07D 311/72* (2013.01); *C07C 2101/16* (2013.01)

(58) Field of Classification Search
CPC ....... C07C 46/06; C07C 403/08; C07D 311/72
USPC ....................................................... 568/362
See application file for complete search history.

(56) References Cited

U.S. PATENT DOCUMENTS

| | | | |
|---|---|---|---|
| 2,856,414 A | 10/1958 | Robeson et al. | |
| 3,406,188 A | 10/1968 | Fletcher | |
| 7,034,054 B2 | 4/2006 | Miller et al. | |
| 7,432,305 B2 | 10/2008 | Miller et al. | |
| 7,470,798 B2 | 12/2008 | Wang et al. | |
| 7,491,312 B2 | 2/2009 | Gilat et al. | |
| 7,514,461 B2 | 4/2009 | Wang et al. | |
| 7,968,746 B2 | 6/2011 | Jankowski et al. | |
| 8,106,223 B2 | 1/2012 | Wesson et al. | |
| 8,314,153 B2 | 11/2012 | Miller et al. | |
| 8,716,486 B2 | 5/2014 | Hinman et al. | |
| 8,716,527 B2 | 5/2014 | Hinman et al. | |
| 8,952,071 B2 | 2/2015 | Hinman et al. | |
| 9,162,957 B2 | 10/2015 | Mollard | |
| 9,278,085 B2 | 3/2016 | Miller et al. | |
| 9,296,712 B2 | 3/2016 | Hinman et al. | |
| 9,370,496 B2 | 6/2016 | Miller | |
| 2004/0116715 A1 | 6/2004 | Baldenius et al. | |
| 2006/0281809 A1 | 12/2006 | Miller et al. | |
| 2010/0105930 A1 | 4/2010 | Wesson et al. | |
| 2010/0222436 A1 | 9/2010 | Miller et al. | |
| 2011/0207828 A1 | 8/2011 | Miller et al. | |
| 2011/0263720 A1 | 10/2011 | Paisley et al. | |
| 2011/0269776 A1 | 11/2011 | Miller et al. | |
| 2013/0109759 A1 | 5/2013 | Miller et al. | |
| 2013/0267538 A1 | 10/2013 | Walkinshaw et al. | |
| 2013/0345312 A1 | 12/2013 | Jankowski et al. | |
| 2014/0031433 A1 | 1/2014 | Miller et al. | |
| 2014/0243424 A1 | 8/2014 | Mollard et al. | |
| 2014/0249160 A1 | 9/2014 | Miller et al. | |
| 2014/0275045 A1 | 9/2014 | Hinman et al. | |
| 2014/0343166 A1 | 11/2014 | Miller et al. | |
| 2015/0057363 A1 | 2/2015 | Miller et al. | |
| 2015/0216820 A1 | 8/2015 | Miller et al. | |
| 2015/0218079 A1 | 8/2015 | Shrader et al. | |
| 2015/0297551 A1 | 10/2015 | Hinman et al. | |
| 2016/0024085 A1 | 1/2016 | Hinman et al. | |
| 2016/0039775 A1 | 2/2016 | Hinman et al. | |
| 2016/0039776 A1 | 2/2016 | Hinman et al. | |
| 2016/0115141 A1 | 4/2016 | Hinman et al. | |

OTHER PUBLICATIONS

John, W. "Cumotocopherol, a new factor of the vitamin E group," Zeitschrift fur physiologische Chemie, 1937, vol. 250, pp. 11-24. (Abstract only in English).
Skinner, W.A., Jr., B.S., M.S., Thesis entitled: "Some Oxidation Products of d1-Alpha-Tocopherol," University of Texas, Austin Texas, 1952, pp. 1-112.
International Search Report mailed on Sep. 28, 2012, for PCT Patent Application No. PCT/US2012/047455 filed on Jul. 19, 2012, pp. 1-2.
International Preliminary Report on Patentability mailed on Jan. 21, 2014, for PCT Patent Application No. PCT/US2012/047455 filed on Jul. 19, 2012, pp. 1-6.
Written Opinion mailed on Sep. 28, 2012, for PCT Patent Application No. PCT/US2012/047445 filed on Jul. 19, 2012, pp. 1-5.
Emmerie et al. "Colorimetric Determination of α-Tocopherol (Vitamin E)," Rec.Trav.Chim., 1938, vol. 57, pp. 1351-1355.
John, W. "Cumotocopherol, a new factor of the vitamin E group," Zeitschrift fur physiologische Chemie, 1937, vol. 250, pp. 11-24.

(Continued)

*Primary Examiner* — Sikarl Witherspoon
(74) *Attorney, Agent, or Firm* — Squire Patton Boggs (US) LLP

(57) ABSTRACT

A method of producing alpha-tocotrienol quinone or a stereoisomer thereof, the method comprising selective opening of alpha-tocotrienol chroman to alpha-tocotrienol quinone in the presence of non-alpha tocotrienol chromans by oxidizing alpha-to-cotrienol with a metal salt oxidizing agent, wherein the stoichiometric ratio of metal salt oxidizing agent/alpha-tocotrienol is at least 4:1 and wherein said metal oxidizing agent is added in sequential additions, in order to reduce oxidation of any amounts of non-alpha tocotrienol chromans that might have been present in the starting alpha-tocotrienol chroman material. This process uses conditions favoring oxidation rates of the alpha tocotrienol chroman vs. the non-alpha tocotrienol chromans.

14 Claims, No Drawings

(56) References Cited

OTHER PUBLICATIONS

Lee Irvin Smith, "The Chemistry of Vitamin E", *School of Chemistry, University of Minnesota,* Minneapolis, Minnesota, Received May 6, 1940, pp. 287-329.
Skinner, W.A., Jr., B.S., M.S., *Ph.D. Thesis entitled*: "Some Oxidation Products of d1-Alpha-Tocopherol," University of Texas, Austin Texas, 1952, pp. 1-112.
International Search Report mailed on Sep. 28, 2012, for PCT Patent Application No. PCT/US2012/047455, filed on Jul. 19, 2012, pp. 1-2.
International Preliminary Report on Patentability mailed on Jan. 21, 2014, for PCT Patent Application No. PCT/US2012/047455, filed on Jul. 19, 2012, pp. 1-6.
Written Opinion mailed on Sep. 28, 2012, for PCT Patent Application No. PCT/US2012/047445, filed on Jul. 19, 2012, pp. 1-5.

METHODS FOR OXIDATION OF ALPHA TOCOTRIENOL IN THE PRESENCE OF NON-ALPHA TOCOTRIENOLS

CROSS REFERENCE TO RELATED APPLICATION

This application is a continuation of U.S. patent application Ser. No. 14/233,734 filed May 19, 2014, which is a 371 of International Application No. PCT/US2012/047455 filed Jul. 19, 2012, which claims benefit of U.S. Provisional Patent Application No. 61/572,645, filed Jul. 19, 2011, the entire contents of which are hereby incorporated by reference for all purposes.

DESCRIPTION

The present invention relates to a method of synthesizing a compound of Formula I:

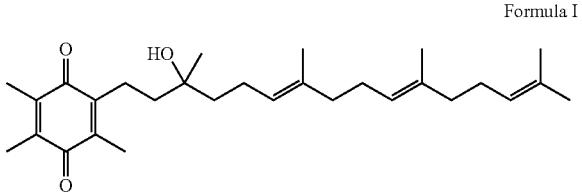 [SMILES: CC(C)=CCC/C(C)=C/CC/C(C)=C/CCC(C)(O)CCC1=C(C)C(=O)C(C)=C(C)C1=O]

Formula I said method comprising selectively oxidizing alpha-tocotrienol in the presence of non-alpha tocotrienols, with a metal salt oxidizing agent to form alpha-tocotrienol of Formula I, wherein the stoichiometric total ratio of the metal salt oxidizing agent/alpha-tocotrienol is selected in a range of at least 4:1 equivalents and said metal oxidizing agent is added in sequential additions. The present process is a method for the selective opening of alpha-tocotrienol chroman to alpha-tocotrienol quinone in the presence of non-alpha tocotrienol chromans that might have been present in the starting alpha-tocotrienol material, using conditions for preferential oxidation of the alpha isomer.

BACKGROUND OF THE INVENTION

Alpha-tocotrienol quinone is under development for the treatment of symptoms associated with mitochondrial diseases. In vitro experiments with alpha-tocotrienol quinone have shown it to be far more potent than COQ10 in enhancing mitochondrial function. (Shrader, W. D.; et al.; *Bioorganic Medicinal Chemistry Letters,* 2011; 21(12): 3693-3698. Preliminary studies have shown it to have some efficacy in patients suffering from mitochondrial diseases such as Friedreich Ataxia, Leigh Syndrome, and Leber's Hereditary Optic Neuropathy (See for example co-assigned applications U.S. application Ser. No. 12/777,179, U.S. application Ser. No. 12/982,716, U.S. application Ser. No. 12/768,565, published as US 2010/0222436, US 2011/0172312, and US 2010/0273894, respectively).

The synthesis of alpha-tocopherol quinone by oxidation of alpha-tocopherol with ferric chloride was first reported in 1937 (John, Z., *Physiol. Chem.,* 250 (1937)). Emmerie and Engels described a procedure to use oxidation with ferric chloride as a quantitative measurement for the amount of alpha-tocopherol in materials (Emmerie and Engel, *Rec. Tray. Chim.,* 57:135 (1938)). Skinner has described some side-products that can occur during oxidation of alpha-tocopherol (Skinner, W. A., Ph.D. Thesis, University of Texas at Austin (1952)). Robeson et al. described and claimed a procedure under improved reaction conditions to produce alpha-tocopheryl quinone free of objectionable amounts of other alpha-tocopherol oxidation products by reacting alpha-tocopherol with ferric chloride in a two-phase solvent reaction medium (U.S. Pat. No. 2,856,414).

However, traditional methods of synthesizing alpha-tocopherol quinone often result in higher than desired concentrations of side-products, mostly when commercial R,R,R-alpha-tocopheryl acetate, invariably contaminated with varying amounts of beta-tocopheryl acetate and gamma-tocopheryl acetate is used. This was disclosed in co-assigned patent application U.S. application Ser. No. 13/044,056 (US 2011/0263720), but nowhere in this application is disclosed the use of special ratios of metal complexes added to the mixture in sequential additions, when the starting material is alpha-tocotrienol containing some non-alpha tocotrienols as impurities. It was also surprising that the oxidation of alpha-tocotrienol required a higher stoichiometric ratio of oxidizing agent than that of alpha tocopherol.

The process used in the production of alpha-tocotrienol as described in co-assigned patent application U.S. application Ser. No. 12/606,923 (US 2010/0105930), may produce amounts of alpha-tocotrienol still containing some, although minimal, amounts of non-alpha tocotrienols that upon oxidation, might give undesirable non-alpha-tocotrienol quinones. The methods of the present invention would improve the purity of the alpha-tocotrienol quinone produced by the synthesis as described in U.S. application Ser. No. 12/606,923 (US 2010/0105930).

BRIEF SUMMARY OF THE INVENTION

The invention is directed to a method of producing a compound of Formula I (alpha tocotrienol quinone):

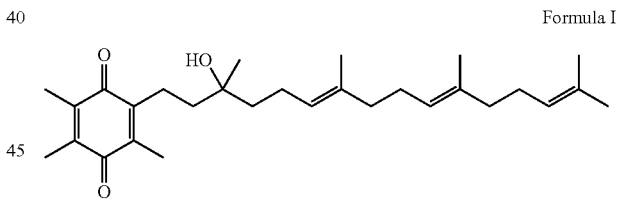

Formula I or a stereoisomer thereof, the method comprising selective opening of alpha-tocotrienol chroman to alpha tocotrienol quinone of Formula I in the presence of non-alpha tocotrienol chromans by oxidizing alpha-tocotrienol with a metal salt oxidizing agent, wherein the stoichiometric ratio of metal salt oxidizing agent/alpha-tocotrienol is at least 4:1 or about 4:1 and wherein said metal oxidizing agent is added in sequential additions.

In some embodiments, the method of producing a compound of Formula I comprises oxidizing alpha-tocotrienol with a metal salt oxidizing agent, in a biphasic solution, wherein the alpha-tocotrienol is dissolved in a non-polar solvent and the metal salt oxidizing agent is dissolved in a polar solvent, and where the separate solutions are mixed to permit the oxidation.

In some embodiments, the metal salt oxidizing agent is an iron(III) salt such as an iron(III) halide, an iron(III) acetate, an iron(III) citrate, an iron(III) nitrate, iron(III) tartrate or an iron(III) phosphate. In some embodiments, the metal salt oxidizing agent is an iron halide such as, e.g., iron (III) chloride (Fe(III)Cl₃). In some embodiments, the metal salt oxidizing agent is serially added in more than one portion. In some embodiments, the method further comprises washing the product with an aqueous solution for removal of metal reagent.

In some embodiments, the stoichiometric ratio of metal salt oxidizing agent/alpha-tocotrienol is at least 4:1. In some embodiments, the metal salt oxidizing agent is added in an amount sufficient to oxidize 70% to 99.9% or about 70% to 99.9% of the alpha-tocotrienol into the alpha-tocotrienol quinone of Formula I. In some embodiments, the metal salt oxidizing agent is sufficient to oxidize at least 98% or at least about 98% of the alpha-tocotrienol chroman into the alpha-tocotrienol quinone of Formula I.

In some embodiments, the invention is directed to a compound of Formula I, made by one of the methods of syntheses described herein. In some embodiments, the compound of Formula I is a compound of Formula Ia:

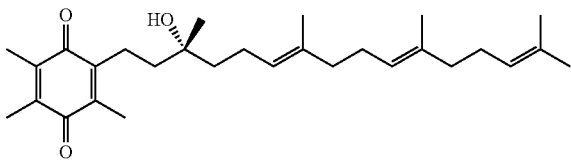

Formula Ia i.e., 2-[(3R,6E,10E)-3-hydroxy-3,7,11,15-tetramethyl-6,10,14-hexadecatrienyl]-3,5,6-trimethyl-2,5-cyclohexadiene-1,4-dione.

In some embodiments, the method of the present invention produces a composition having less than 1% or less than about 1% of one of the non-alpha tocotrienol quinones relative to the compound of Formula I. In some embodiments, the composition has less than 0.7% or less than about 0.7% of one of the non-alpha tocotrienol quinone, or less than 0.2% of one of the non-alpha tocotrienol quinone relative to the compound of Formula I. In some embodiments, the amount of compound of Formula I in the composition of the present invention is greater than 70% (wt/wt) or greater than about 70% of the composition. In some embodiments, the amount of compound of Formula I in the composition of the present invention is greater than 80% (wt/wt) or greater than about 80% of the composition.

In some embodiments, the amount of compound of Formula I in the composition of the present invention is greater than 90% (wt/wt) or greater than about 90% of the composition. In some embodiments, the amount of compound of Formula I in the composition of the present invention is greater than 95% (wt/wt) or greater than about 95% of the composition. In some embodiments, the amount of compound of Formula I in the composition of the present invention is greater than 97% (wt/wt) or greater than about 97% of the composition. In some embodiments, the amount of compound of Formula I in the composition of the present invention is greater than 99% (wt/wt) or greater than about 99% of the composition. In some embodiments, the amount of compound of Formula I in the composition of the present invention is greater than 99.5% (wt/wt) or greater than about 99.5% of the composition.

In some embodiments, the composition has less than 10% (wt/wt) or less than about 10% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 5% (wt/wt) or less than about 5% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 2.5% (wt/wt) or less than about 2.5% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 1% (wt/wt) or less than about 1% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 0.5% (wt/wt) or less than about 0.5% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 0.2% (wt/wt) or less than about 0.2% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof.

In some embodiments, the composition has less than 10% (wt/wt) or less than about 10% of non-alpha-tocotrienol quinone compounds selected from beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 5% (wt/wt) or less than about 5% of non-alpha-tocotrienol quinone compounds selected from beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 2.5% (wt/wt) or less than about 2.5% of non-alpha-tocotrienol quinone compounds selected from beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 1% (wt/wt) or less than about 1% of non-alpha-tocotrienol quinone compounds selected from beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 0.5% (wt/wt) or less than about 0.5% of non-alpha-tocotrienol quinone compounds selected from beta-tocotrienol, beta-tocotrienol quinone, gamma-tocotrienol, gamma-tocotrienol quinone, delta-tocotrienol, delta-tocotrienol quinone, or combinations thereof. In some embodiments, the composition has less than 0.2% (wt/wt) or less than about 0.2% of non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof.

In some embodiments, the method of the present invention further comprises adding a pharmaceutically acceptable excipient to the compound of Formula I made by the methods of the present invention. In some embodiments, the invention is directed to an oral dosage form comprising the compound of Formula I, made by the method of the present invention.

The present invention is also directed to a method of treating a mitochondrial disorder, modulating one or more energy biomarkers, normalizing one or more energy biomarkers, or enhancing one or more energy biomarkers, the method comprising administering to a subject a therapeutically effective amount or effective amount of a composition made by the methods of the present invention, the composition comprising a compound of Formula I or a stereoisomer thereof, for example a compound of Formula Ia, wherein the composition has less than 10% (mol/mol) (or less than about 10%), less than 5% (mol/mol) (or less than about 5%), than 2% (mol/mol) (or less than about 2%), less than 1% (mol/mol) (or less than about 1%), or less than 0.5% (mol/mol) (or less than about 0.5%), or less than 0.2% (mol/mol) (or less than about 0.2%)of non-alpha tocotrienol quinones relative to the compound of Formula I.

In some embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber Hereditary Optic Neuropathy (LHON); Leigh Disease; Kearns-Sayre Syndrome (KSS); Friedreich Ataxia (FA); other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; other neurological diseases; epilepsy; genetic diseases; Huntington's Disease; mood disorders; schizophrenia; bipolar disorder; age associated diseases; macular degeneration; diabetes; and cancer. In some embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); and Friedreich's Ataxia (FA).

In some embodiments, the energy biomarker is selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H) levels; NADPH (NADPH+H) levels; NAD levels; NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'deoxyguanosine(8-OHdG) levels; levels of reactive oxygen species; levels of oxygen consumption (VO2); levels of carbon dioxide output (VCO2); respiratory quotient (VCO2NO2); exercise tolerance; and anaerobic threshold.

In some embodiments, the subject is selected from the group consisting of: a subject with a mitochondrial disease; a subject undergoing strenuous or prolonged physical activity; a subject with chronic energy problems; a subject with chronic respiratory problems; a pregnant female; a pregnant female in labor; a neonate; a premature neonate; a subject exposed to an extreme environment; a subject exposed to a hot environment; a subject exposed to a cold environment; a subject exposed to an environment with lower-than-average oxygen content; a subject exposed to an environment with higher-than-average carbon dioxide content; a subject exposed to an environment with higher-than-average level of air pollution; a subject with lung disease; a subject with lower-than-average lung capacity; a tubercular patient; a lung cancer patient; an emphysema patient; a cystic fibrosis patient; a subject recovering from surgery; a subject recovering from illness; a subject undergoing acute trauma; a subject in shock; a subject requiring acute oxygen administration; a subject requiring chronic oxygen administration; an elderly subject; an elderly subject experiencing-decreased energy; and a subject suffering from chronic fatigue.

DETAILED DESCRIPTION OF THE INVENTION

The present invention is directed to a method for limiting the formation of non-alpha tocotrienol quinones through control of the stoichiometric ratio of the metal salt oxidizing agent. The present invention is directed to using the rate of reaction of alpha-tocotrienol with metal salt oxidizing agent that is faster than the rate of reaction of any of the non-alpha tocotrienols to selectively oxidize alpha-tocotrienol, comprising some non-alpha tocotrienols, to alpha-tocotrienol quinone, and using a stoichiometric ratio of metal salt oxidizing agent to starting material that is essential to the completion of the reaction.

The oxidation process according to the present invention uses an amount of metal salt oxidizing agent, so that some of the tocotrienols are not oxidized before the metal salt oxidizing agent is exhausted, preferential oxidation of the alpha-isomer can be achieved.

Synthesis

The present invention is directed to a method of synthesizing alpha-tocotrienol quinone of Formula I:

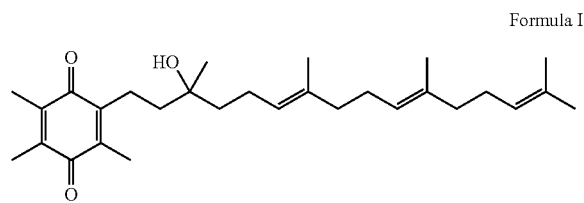 [SMILES: CC(C)=CCC/C(C)=C/CC/C(C)=C/CCC(C)(O)CCC1=C(C)C(=O)C(C)=C(C)C1=O]

Formula I or a stereoisomer thereof, the method forming a reduced or non-detectable amount of non-alpha tocotrienol quinones.

In some embodiments, the method comprises oxidizing alpha-tocotrienol with a metal salt oxidizing agent to form the compound of Formula I, wherein the stoichiometric ratio (mol/mol) of metal salt oxidizing agent/alpha-tocotrienol is at least 4:1 or about 4:1.

The alpha-tocotrienol starting material employed in the present invention can be isolated from various organisms, or can be chemically synthesized. In some embodiments, alpha-tocotrienol is isolated from a plant extract, e.g., palm oil, rice bran oil, barley and annatto beans. Tocotrienols occur largely in palm oil, rice bran oil and barley. Crude palm oil which is rich in tocotrienols (800-1500 ppm) offers a potential source of natural tocotrienols. Carotech, Malaysia is the only industrial plant in the world that is able to extract and concentrate tocotrienols from crude palm oil.

Carotech uses a molecular distillation process (with ultra-high vacuum, super low temperature) in its integrated production plant. This unique process patented in U.S. Pat. No. 5,157,132; allows Carotech to extract valuable phytonutrients, specifically the Tocotrienol Complex (Tocomin®), from the crude palm oil. Tocomin®-50 typically comprises about 25.32% mixed tocotrienols (7.00% alpha-tocotrienol, 14.42% gamma tocotrienol, 3.30% delta tocotrienol and 0.6% beta tocotrienol), 6.90% alpha-tocopherol and other phytonutrients such as plant squalene, phytosterols, co-enzyme Q10 and mixed carotenoids. The alpha-tocopherol and other phytonutrients can be separated from the mixed tocotrienols of this complex by the process described in co-assigned application U.S. application Ser. No. 12/606,923.

In another embodiment, the starting tocotrienols of the present invention comprise an enriched tocotrienol extract from palm oil, as sold by Carotech, Golden Hope Bioorganic, Carotech, Davos Life Science, Beijing Gingko Group, Eisai, Eastman Corporation, Sime Darby Biorganic Sdn Bhd or Palm Nutraceuticals enriched by the co-assigned application U.S. application Ser. No. 12/606,923.

Tocotrienols from crude palm oil which is rich in tocotrienols (800-1500 ppm) can also be extracted using a molecular distillation process (with ultra-high vacuum, super low temperature) in its integrated production plant, patented in U.S. Pat. No. 5,157,132.

Other isolation processes of tocotrienols are for instance A. G. Top et al., U.S. Pat. No. 5,190,618 (1993); Tanaka, Y. et al, Japanese Patent No. JP2003-171376 (2003); M. Kitano et al., Japanese Patent No. 2003-02777 (2003) or Burger et al., U.S. Pat. No. 4,603,142.

Syntheses of various members of the tocotrienol family in the d,l- or (RS)-form have been published, see for example Schudel et al., Helv. Chim. Acta (1963) 46, 2517 2526; H. Mayer et al., Helv. Chim. Acta (1967) 50, 1376 11393; H.-J. Kabbe et al., Synthesis (1978), 888 889; M. Kajiwara et al., Heterocycles (1980) 14, 1995 1998; S. Urano et al., Chem. Pharm. Bull. (1983) 31, 4341 4345, Pearce et al., J. Med Chem. (1992), 35, 3595 3606 and Pearce et al., J. Med. Chem. (1994). 37, 526 541. None of these reported processes lead to the natural form of the tocotrienols, but rather produce racemic mixtures. Syntheses of natural form d-tocotrienols have been published. See for example. J. Scott et al., Helv. Chim. Acta (1976) 59, 290 306, Sato et al. (Japanese Patent 63063674); Sato et al. (Japanese Patent No. JP 01233278) and Couladouros et at (U.S. Pat. No. 7,038,067).

Pure members of the tocotrienol family have also been produced by expensive procedures such as preparative scale reversed-phase chromatography or simulated moving bed chromatography. For some examples of such isolation and purification processes, see for instance Top A. G. et al., U.S. Pat. No. 5,190,618; Lane R. et al., U.S. Pat No. 6,239,171; Bellafiore, L. et at U.S. Pat. No. 6,395,915; May, C. Y. et al., U.S. Pat. No. 6,656,358; Jacobs, L et al., U.S. Pat. No. 6,838,104; Sumner, C. et al. Int. Pat. Pub. WO 99/38860, or Jacobs, L., Int. Pat. Pub. WO 02/500054.

Any of those procedures may be used for the production of the starting material of this invention which may be still contaminated with non-alpha tocotrienols.

A metal salt oxidizing agent is added to the starting alpha-tocotrienol obtained by any procedure described above or any other procedure known to the skilled in the art to facilitate the oxidation of the alpha-tocotrienol to a compound of Formula I. Metal salt oxidizing agents are known to those in the art, and can include, but are not limited to transition metals with halides, e.g., chromium halides, manganese halides, iron halides, copper halides, palladium halides, silver halides, cadmium halides, and the like; transition metal oxides, e.g., silver oxide; permanganate ions; ferricyanide ions; nitric acid; iodine; bromine; hypochlorite; peroxides, and oxygen with a free radical initiator. In some embodiments, an electrochemical cell can be used in place of a metal salt oxidizing agent to oxidize alpha-tocotrienol. One of skill in the art can calculate the time and energy required for an electrochemical cell to achieve an amount of oxidation comparable to the methods of synthesis described herein. The term "halides" refer to a halogen atom ion bearing a negative charge, the halide anions selected from the group consisting of fluoride (F—), chloride (Cl—), bromide (Br—), and iodide (I—).

Thus, the term metal salt oxidizing agent can include, e.g., FeCl3. In some embodiments, the metal salt oxidizing agent is dissolved in a solvent solution, e.g., the metal salt oxidizing agent is in an aqueous solution, e.g., water or a water/alcohol solution.

The metal salt oxidizing agent can be added to alpha-tocotrienol solution in various ways. For example, the metal salt oxidizing agent can be added to the solution at a single point in time, in a single portion, and/or stirred by mechanical mixing for the duration of the oxidation reaction. In some embodiments, the metal salt oxidizing agent can be added to the product of the hydrolysis reaction slowly over a prolonged period of time, e.g., over 1, 2, 10, 15, 20, or 30 minutes. Alternatively, the metal salt oxidizing agent can be added in multiple portions, i.e., serial additions or aliquots, wherein the metal salt oxidizing agent is added and the mixture is allowed to settle. In some embodiments, the aqueous layer is removed prior to addition of the next portion of metal salt oxidizing agent.

In some embodiments, four portions are added, with the aqueous layer being removed before addition of any subsequent portions of metal salt oxidizing agent.

In some embodiments, the alpha-tocotrienol quinone solution resulting from the addition of the metal salt oxidizing agent can be washed one or more times with an aqueous wash, e.g., water, buffer (e.g., sodium bicarbonate), or other aqueous solutions,(e.g., an aqueous salt solution, i.e., sodium or potassium chloride), to remove impurities and the metal salt oxidizing agent. For example, an aqueous wash can be performed at the termination of the oxidation reaction. In some embodiments, one or more washes are used, e.g., 2, 3, 4, 5 or more washes are used. The wash can then be discarded, or alternatively, can be recycled and/or reused.

In some embodiments, an aqueous wash is performed prior to addition of one or more portions of metal salt oxidizing agent, and the aqueous layer is removed to waste between each portion.

Unless designated otherwise, the term "stoichiometric ratio" refers to the total ratio of the moles of metal salt oxidizing agent relative to the moles of alpha-tocotrienol in the oxidation reaction. Thus, for a stoichiometric ratio in an oxidation reaction which includes serial additions of multiple portions of metal salt oxidizing agent, the term stoichiometric ratio would refer to the total additive amount of moles of metal salt oxidizing agent in all the multiple portions added to the oxidation reaction.

In some embodiments, the stoichiometric ratio is 4 to 1; 4.5 to 1; 5 to 1; or 5.5 to 1. In some embodiments, the stoichiometric ratio of metal salt oxidizing agent/alpha-tocotrienol is 4 to 1 or 4.5 to 1. In some embodiments, the oxidation reaction contains serial additions of multiple portions of metal salt oxidizing agent, wherein the individual portion of metal salt oxidizing agent contains a stoichiometric ratio of metal salt oxidizing agent/alpha-tocotrienol of greater than 1, greater than 2, greater than 3, greater than 4 or greater than 5.0. In some embodiments, the stoichiometric ratio of metal salt oxidizing agent/alpha-tocotrienol in each individual portion is 0.2 to 1; 0.4 to 1; 0.5 to 1; 0.6 to 1; 0.7 to 1; 0.75 to 1; 0.8 to 1; 0.9 to 1; 1.0 to 1; 1.2 to 1; 1.4 to 1; 1.6 to 1; 2 to 1; 2.5 to 1; 3.0 to 1; 3.5 to 1; 4.0 to 1; 4.5 to 1 or 5.0 to 1. For example, in some embodiments, three or four portions of metal salt oxidizing agent are used, each portion having a stoichiometric ratio of metal salt oxidizing agent/alpha-tocotrienol in each individual portion of 1 to 1; 1.5 to 1; 2.0 to 1; or 2.5 to 1.

In some embodiments, multiple portions of metal salt oxidizing agent are used, each portion having a stoichiometric ratio of metal salt/oxidizing agent/alpha-tocotrienol, where individual portions with a ratio of 1.0 to 1.0 are used. In some embodiments, multiple portions of metal salt oxidizing agent are used, each portion having a stoichiometric ratio of metal salt/oxidizing agent/alpha-tocotrienol, with a ratio of 1.5 to 1.0 are used. In some embodiments, four portions of metal salt oxidizing agent are used, each portion having a stoichiometric ratio of metal salt/oxidizing agent/alpha-tocotrienol, with a ratio of 1.0 are used. In some embodiments, three portions of metal salt oxidizing agent are used, each subsequent portion having a decreased stoichiometric ratio of metal salt/oxidizing agent/alpha-tocotrienol, e.g., the first portion has a ratio of 2.0, the second portion has a ratio of 1.5, and the third portion has a ratio of 0.5. Alternatively, four portions of metal salt oxidizing agent are used, each subsequent portion having a decreased stoichiometric ratio of metal salt/oxidizing agent/alpha-tocotrienol, e.g., the first portion has a ratio of 1.5, the second portion has a ratio of 1.25, the third portion has a ratio of 0.75 and the fourth portion has a ratio of 0.5.

In some embodiments, the metal salt oxidizing agent is added in an amount sufficient to oxidize 70% to 99.9% (mol/mol) of the alpha-tocotrienol to the compound of Formula I. In some embodiments, the metal salt oxidizing agent is added in an amount sufficient to oxidize 75%, 85%, 87%, 90%, 92%, 95%, 97%, 98%, 99%, 99,5% or 99.9% to the compound of Formula I.

Oxidation of alpha-tocotrienol can be carried out by adding a metal salt, e.g., ferric chloride, to the alpha-tocotrienol. In some embodiments, the oxidation is carried out in a biphasic solution of alpha-tocotrienol dissolved in a mixture of alcohol and/or ether, and metal salt dissolved in water or a mixture of water and alcohol. The alpha-tocotrienol can be dissolved in methanol, ethanol, ether or acetone, with the metal salt, with or without water. In some embodiments, the reaction proceeds in a homogeneous solution. In other embodiments, the alpha-tocotrienol and the metal salt are mixed in a biphasic system: (i) an organic phase consisting predominantly of alpha-tocotrienol, and/or alpha-tocotrienol quinone dissolved in non-polar solvent(s) e.g. in alcohol/ether, and (ii) a predominantly aqueous phase containing ferric/ferrous chlorides. In other embodiments, oxidation of alpha-tocotrienol can be carried out by dissolving alpha-tocotrienol in a 1:2 mixture of ethanol and methyl tert-butyl ether (MTBE), and dissolving the metal salt in water or a mixture of water and ethanol, preferably 2:1 of water: ethanol.

In the two phase reaction system, the metal salt can be serially added in multiple portions, wherein a first portion of metal salt is added, followed by removal of the polar phase of the first portion and addition of subsequent portions of metal salt solution. Using serial portion addition, the metal salt of the first portion oxidizes the alpha-tocotrienol and the spent oxidizer enters in the aqueous phase and is predominantly removed to waste before addition of the subsequent portion.

The oxidation reaction can be allowed to proceed until the alpha-tocotrienol is almost completely oxidized. The reaction can be checked for completeness by sampling and analyzing the batch by means known to those in the art, e.g., by HPLC. In some embodiments, the reaction is complete when alpha-tocotrienol is less than about 30%, less than about 25%, less than about 20%, less than about 15%, less than about 10%, less than about 5%, less than about 4%, less than about 3%, less than about 2%, less than about 1%, less than about 0.5% or less than about 0.2% area percent at 205 nm as measured by HPLC. In some embodiments, the sample is analyzed by HPLC using a C6-Phenyl column (Phenomenex, Torrance, Calif.) eluted with a mixture of acetonitrile and water.

Alternatively, the oxidation reaction can be allowed to proceed, while measuring the formation of one or more of the undesired side-products. Since it has been found that there exists selective oxidation during the oxidation of alpha-tocotrienol to alpha-tocotrienol quinone, the oxidation reaction can be allowed to proceed while measuring the formation of non-alpha tocotrienol quinones.

In some embodiments, the oxidation reaction is allowed to proceed while measuring the formation of one or more of the undesired side-products and interrupted when one or more of the undesired side-products are detected. For example, one or more side-products are produced at a relatively reduced rate relative to the production of alpha-tocotrienol quinone at the beginning of the oxidation reaction. Thus, in some embodiments, the oxidation reaction can be allowed to proceed until the level of the side-products reaches a pre-determined level, e.g., 10%, 8%, 6%, 5%, 4%, 3%, 2%, 1% , 0.5% or 0.25% area percent at 261 nm as measured by HPLC. In some embodiments, no single side product greater than 1%, greater than 0.5%, or greater than 0.25% area percent at 261 nm as measured by HPLC. These undesired side-products can include, but are not limited to non-alpha tocotrienol quinones such as beta-tocotrienol quinone, gamma-tocotrienol quinone, delta-tocotrienol quinone, and combinations thereof.

In some embodiments, the side-product is gamma-tocotrienol quinone. In some embodiments, the side-product is delta-tocotrienol quinone. In some embodiments, the side-product is beta-tocotrienol quinone. In some embodiments, the reaction is considered to be complete when one or more of the side-products is less than about 2%, less than about 1.5%, less than about 1.0%, less than about 0.75%, less than about 0.5%, less than about 0.25% or less than about 0.1% area percent at 261 nm as measured by HPLC.

Various means can be used to purify the alpha-tocotrienol quinone from any solvents which can be present. Solvent extraction methods are known in the art. For example, in some embodiments, selective evaporation can be used to evaporate the solvent. In some embodiments, a rotary evaporator can be used to remove the solvent under vacuum. In some embodiments, the compound of Formula I is placed in an organic solvent such as n-heptane for storage and/or further processing.

In some embodiments, a metal chelating agent is used. Examples of metal chelating agents are known to those in the art and can include acrylic polymers, ascorbic acid, tetrasodium iminodisuccinate, citric acid, dicarboxymethylglutamic acid, ethylenediaminedisuccinic acid (EDDS), ethylenediaminetetraacetic acid (EDTA), methylene phosphonic acid), malic acid, or nitrilotriacetic acid (NTA). Additional means can be used to separate various undesired side-products, as well as the reaction material, the techniques including, but not limited to silica columns.

Compositions

In some embodiments, the invention is directed to a method of synthesizing a compound of Formula I:

Formula I

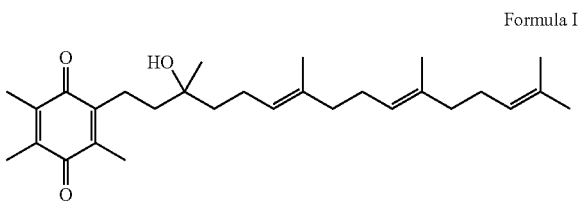 [SMILES: CC(C)=CCC/C(C)=C/CC/C(C)=C/CCC(C)(O)CCC1=C(C)C(=O)C(C)=C(C)C1=O]

or a stereoisomer thereof, wherein the synthesis results in a composition having less than 2%, less than 1.5%, less than 1.0%, less than 0.8%, less than 0.6%, less than 0.4%, or less than 0.2% (mol/mol) non-alpha tocotrienol quinone relative to the compound of Formula I. The invention also includes all stereoisomers of the compounds, including diastereomers, enantiomers and cis-trans isomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated. In some embodiments, the compound of the present invention can be in the R conformation, with all trans double bonds as described by Formula Ia:

Formula Ia

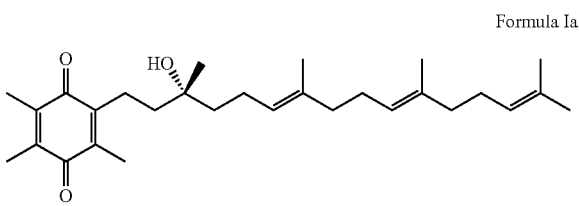 [SMILES: CC(C)=CCC/C(C)=C/CC/C(C)=C/CC[C@@](C)(O)CCC1=C(C)C(=O)C(C)=C(C)C1=O]

i.e., 2-[(3R,6E,10E)-3-hydroxy-3,7,11,15-tetramethyl-6,10,14-hexadecatrienyl]-3,5,6-trimethyl-2,5-cyclohexadiene-1,4-dione.

In some embodiments, a single stereoisomer is present in the composition of the present invention. In some embodiments, at least 70%, at least 80%, at least 90%, at least 95%, or at least 99% (mol/mol) of the compounds of Formula I present in the composition of the present invention have the same stereochemistry. In some embodiments, the compounds of Formula I present in the composition of the present invention are in a racemic mixture.

The present invention can be directed to a method of synthesizing compositions having low amounts of non-alpha tocotrienol quinones.

The term "non-alpha tocotrienol(s)" refers to one or more tocotrienols selected from beta-tocotrienol, gamma-tocotrienol, delta-tocotrienol and mixtures or stereoisomers thereof, wherein beta-tocotrienol, gamma-tocotrienol and delta-tocotrienol have the structures described below.

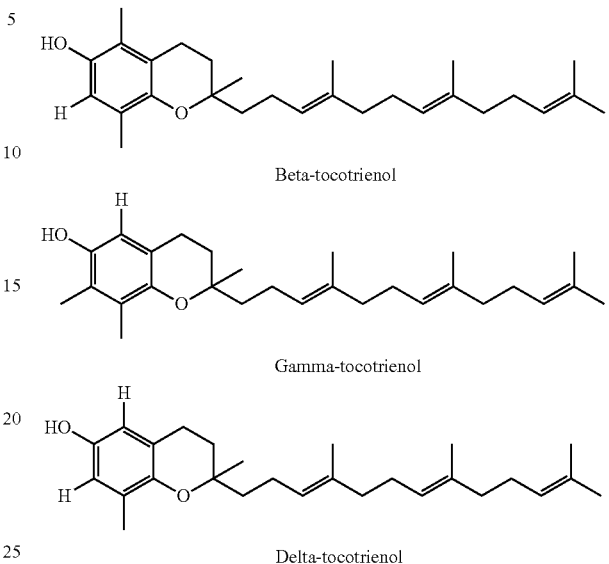

The term "non-alpha tocotrienol quinone(s)" refers to one or more tocotrienol quinones selected from beta-tocotrienol quinone, gamma-tocotrienol quinone, delta-tocotrienol quinone, and mixtures or stereoisomers thereof, wherein beta-tocotrienol quinone, gamma-tocotrienol quinone and delta-tocotrienol quinone have the structures described below.

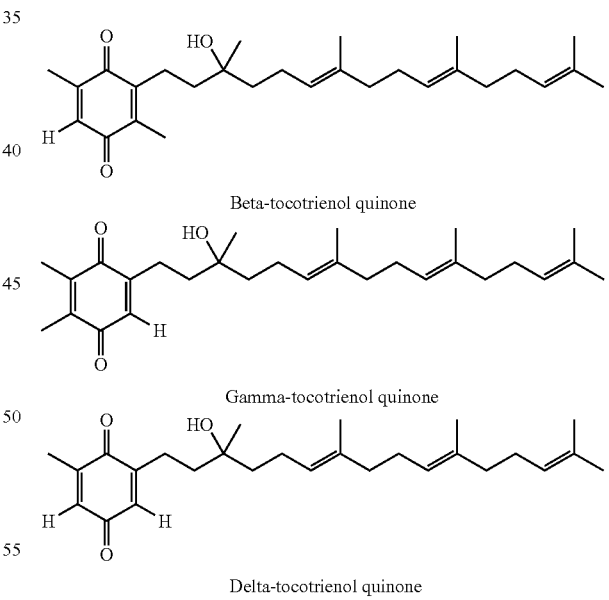

Compositions described herein can contain various amounts of one or more non-alpha tocotrienol quinones. In some embodiments, the composition has less than 2.0%, less than 1.5%, less than 1.0%, less than 0.8%, less than 0.6%, less than 0.4%, or less than 0.2% (mol/mol) of one or more non-alpha tocotrienol quinones relative to the compound of Formula I. In some embodiments, the composition has less than 0.2% (mol/mol) of one non-alpha-tocotrienol quinone relative to the compound of Formula I. In some embodiments, the composition has less than 0.15% (mol/mol) of one non-alpha tocotrienol quinone relative to the compound of Formula I. In some embodiments, the composition has less than 0.1% (mol/mol) of one non-alpha tocotrienol quinone relative to the compound of Formula I. In some embodiments, one or more non-alpha tocotrienol quinones are not detected in the composition using techniques currently known in the art.

Methods of Using

In some embodiments, the compound of Formula I produced by the methods of the present invention can be used to treat one or more conditions in a subject. The composition can comprise other materials and compounds in addition to the compound of Formula I.

One of skill in the art can recognize that various excipients, flavorings, colorants, and/or rate-releasing agents can be added to the composition. In some embodiments, the composition is a pharmaceutically acceptable composition. In some embodiments, the composition further comprises pharmaceutically acceptable excipients. As used herein, "excipient" refers to a substance, or mixture of substances, that is used in the formulation of compositions of the present invention, to give desirable physical characteristics to the formulation. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In some embodiments, the term "pharmaceutically acceptable" means approved by a regulatory agency of the Federal or a state government or listed in the U.S. Pharmacopeia (2009) or other generally recognized international pharmacopeia for use in animals, and more particularly in humans. Various pharmaceutically acceptable excipients can be used. In some embodiments, the pharmaceutically acceptable excipient can be, but is not limited to, a stiffening agent, a solvent, an emulsifier, a buffering agent, a filler, an emollient, a stabilizer, or combinations thereof.

The term "stiffening agent" refers to a substance, or mixture of substances, added to make the composition more viscous at room temperature. In some embodiments, a stiffening agent is any substance that promotes formation of a formulation having a semisolid or solid consistency. The stiffening agent can be hydrophilic (e.g., carbopol, carboxymethylcellulose, hydroxypropylmethylcellulose, alginate, polyethylene glycol).

In some embodiments, the stiffening agent has low hydrophilic-lipophilic balance (HLB). Examples of suitable stiffening agents include, but are not limited to, hydrogenated vegetable oil, cetyl alcohol, cetyl esters wax, microcrystalline wax, paraffin, stearyl alcohol, lauryl alcohol, myristal alcohol, cetostearyl alcohol, white wax, yellow wax, beeswax, candelilla wax, cotton wax, carnauba wax, bayberry wax, rice-bran wax, and combinations thereof.

The term "solvent" refers to any substance capable of dissolving or dispersing the compound of Formula I produced by the methods of the present invention or one or more of the excipients. The solvent can be lipophilic.

In some embodiments, the solvent is lipophilic, and is 2% to 50% by weight, or 5% to 20% by weight, of the total composition. In some embodiments, the solvent is an oil, such as vegetable, nut, and seed oils (e.g., almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower-seed oil, wheat germ oil, and cocoa butter), or hydrocarbon and petroleum oils (e.g., petrolatum, mineral oil, and liquid paraffin).

In some embodiments, the composition of the present invention comprises an emulsifier. The term "emulsifier" refers to any substance that promotes formation and stabilization of an emulsion or suspension. In some embodiments, the emulsifier includes, but is not limited to, sodium lauryl sulfate, propylene glycol mono stearate, methyl stearate, glyceryl monostearate, and combinations thereof.

The term "buffering agent" refers to any substance capable of neutralizing both acids and bases and thereby maintaining the desired pH of the composition of the present invention. In some embodiments, the buffering agent affects the emulsifying properties.

In some embodiments, the buffer can be, but is not limited to, Tris buffers (Tris EDTA (TE), Tris acetate (TAE), Tris phosphate (TPE), Tris glycine), phosphate buffers (e.g., sodium phosphate, potassium phosphate), bicarbonate buffers, acetate buffers (e.g., sodium acetate), ammonium buffers, citrate buffers, and derivatives and combinations thereof. In some embodiments, an organic acid buffer is used. In some embodiments, an acetate buffer, a phosphate buffer, or a citrate buffer can be used. In some embodiments, a zwitterionic buffer can be used. In some embodiments, the buffering agent is a phosphate buffer (e.g., sodium phosphate dibasic).

The pH of the composition of the invention can be physiologically compatible and/or sufficient to maintain stability of the composition. In some embodiments, the composition of the present invention can have a pH of about 5 to about 9, or a pH of about 6.5 to about 8.

As defined herein, "filler" is a substance used to give bulk to the composition without chemically reacting with the compound of Formula I. Fillers are known to those in the art, see e.g., Remington: The Science and Practice of Pharmacy, $21^{st}$ ed. (2005). The concentration of the compound of Formula I in the composition of the present invention can vary. For example, in some embodiments, the amount of compound of Formula I produced by the methods of the present invention is greater than 40%, greater than 45%, greater than 50%, greater than 60%, greater than 70%, greater than 75%, greater than greater than 80%, greater than 90% or greater than 95% (wt/wt) of the composition of. In some embodiments, the compound of Formula I produced by the methods of the present invention is about 40% to about 60% (wt/wt) of the composition. In some embodiments, the composition comprising about 40% to about 60% (wt/wt), or about 50% (wt/wt) of the compound of Formula I produced by the methods of the present invention is placed in a capsule, e.g., a gelatin capsule.

As used herein, "administering" refers to placing or delivering a pharmaceutically effective amount of the compound of Formula I to the subject being treated. Examples of such administration include providing the desired active agent by routes, such as, but not limited to, parenterally, subcutaneously, intravenously, intramuscularly, transdermally, buccally, or orally. For example, composition of the present invention can be administered via solid oral dosage forms which include, but are not limited to, tablets, caplets, coated tablets, capsules, cachets, pellets, pills, powders, granules, syrups, slurries, and liquids; topical dosage forms which include, but are not limited to, transdermal patches, powders, fluid emulsions, fluid suspensions, semi-solids, ointments, pastes, creams, gels and jellies, and foams; and parenteral dosage forms which include, but are not limited to, solutions, suspensions, emulsions, and dry powder. The means and methods for administration are known in the art and an artisan can refer to various pharmacologic references for guidance. For example, "Modem Pharmaceutics," Banker & Rhodes, Marcel Dekker, Inc., 4th ed. (2002); and "Goodman & Gilman's The Pharmaceutical Basis of Therapeutics," 10th ed., MacMillan Publishing Co., New York 2001 can be consulted.

In some embodiments, the composition is administered orally, e.g., the composition can be administered via an oral dosage form. The dosage form can include, e.g., a push-fit capsule, or a soft sealed capsule. In some embodiments, the capsule is made of gelatin, or gelatin and a plasticizer, such as glycerol or sorbitol. The push-fit capsules-can contain the active ingredients in admixture with filler such as, e.g., oils, lactose, binders such as, e.g., starches, and or lubricants such as, e.g., talc or magnesium stearate and or stabilizers. In soft capsules, the compound of Formula I produced by the methods of the present invention can be dissolved or suspended in suitable liquids, such as fatty oils, liquid paraffin, or liquid polyethylene glycols. In some embodiments, oral administration is accomplished by administering to the subject a liquid dosage form. Liquid dosage forms for oral administration can include pharmaceutically acceptable emulsions, solutions, suspensions, syrups, and elixirs containing inert diluents commonly used in the art, such as water. The composition can also be administered in liposome formulations. In some embodiments, oral administration is accomplished by administering to the subject a solid oral dosage form. Solidifying agents are known in the art, and can include, e.g., polyethylene glycol glycerides composed of mono-, di-, and triglycerides, and mono- and diesters of polyethylene glycol (Gelucire®, Gattefosse Canada, Montreal, Canada) and Neusilin® (magnesium aluminometasilicate; Fuji Chemical Co., Japan). All compositions for oral administration should be in dosages suitable for such administration.

The composition of the present invention can also be administered transdermally.

Transdermal administration of the composition of the present invention can be applied to a plaster or transdermal patches, both of which are known in the art, for prolonged delivery across the skin. Devices or systems known to the art include reservoir type devices involving membranes that control the rate of drug release to the skin and devices involving a dispersion of the drug in a matrix.

The composition can also be administered in parenteral dosage forms, i.e., via intravenous, intraarterial, intramuscular, or intraperitoneal dosage forms. Parenteral preparations, for example, sterile injectable aqueous or oleaginous suspensions, can be formulated according to the known art using suitable dispersing or wetting agents and suspending agents. The sterile injectable preparation can also be a sterile injectable solution or suspension in a nontoxic parenterally acceptable diluent or solvent, for example, as a solution in propylene glycol. Among the acceptable vehicles and solvents that can be employed are water, Ringer's solution, and isotonic sodium chloride solution.

In addition, sterile fixed-oils are conventionally employed as a solvent or suspending medium. For this purpose any bland fixed-oil can be employed including synthetic mono- or diglycerides. In addition, fatty acids such as oleic acid find use in the preparation of injectables.

The amount of active ingredient that can be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The therapeutically effective amount or effective amount for a given situation can be readily determined by routine experimentation and is within the skill and judgment of the ordinary clinician.

In some embodiments, an "effective amount" of a compound of Formula I is an amount of the compound of Formula I produced by the methods of the present invention sufficient to modulate, normalize, or enhance one or more energy biomarkers. A "therapeutically effective amount" of a compound of Formula I is an amount of the compound of Formula I produced by the methods of the present invention, which, when administered to a subject, is sufficient to reduce or eliminate either a disease or one or more symptoms of a disease, or to retard the progression of a disease or one or more symptoms of a disease, or to reduce the severity of a disease or one or more symptoms of a disease, or to suppress the clinical manifestation of a disease, or to suppress the manifestation of adverse symptoms of a disease. A therapeutically effective amount can be given in one or more administrations.

An "effective amount" of a compound embraces both a therapeutically effective amount, as well as an amount effective to modulate, normalize, or enhance one or more energy biomarkers in a subject.

The term "daily dosage," "daily dosage level," "daily dosage amount," or "daily dose" means the total amount of the compound of Formula I (or a stereoisomer thereof) produced by the methods of the present invention, administered per day. Thus, for example, administration of a compound of Formula I to a subject at a "daily dosage amount of 300 mg" means that the subject receives a total of 300 mg of the compound produced by the methods of the present invention on a daily basis, whether the compound is administered as a single 300 mg dose or, e.g., three separate 100 mg doses. Conventional means of administering the compound of Formula I can be as a single dose, a twice daily dosing, three times daily dosing, or four times daily dosing. The term "once daily" or "daily" refers to administration of a composition of the present invention once during a 24 hour period.

Daily dosage amounts of the compound of Formula I produced by the methods of the present invention can vary, but can include, e.g., about 0.5 µg/kg to about 200 mg/kg body weight, or about 1.0 µg/kg to about 100 mg/kg body weight, or about 2.0 µg/kg to about 50 mg/kg body weight, or about 3.0 µg/kg to about 10 mg/kg body weight, or about 100.0 µg/kg to about 10 mg/kg body weight, or about 1.0 mg/kg to about 10 mg/kg body weight, or about 10 mg/kg to about 100 mg/kg body weight, or about 50 mg/kg to about 150 mg/kg body weight, or about 100 mg/kg to about 200 mg/kg body weight, or about 150 mg/kg body weight.

In some embodiments, various administration regimens can be used to achieve the desired beneficial effects. In some embodiments, the composition of the present invention is administered for treatment of a chronic disease, and thus is administered at least once daily for the remainder of the subject's lifetime, or from 1 to 20 years, or 1, 2, 5, 10, or 15 years. In some embodiments, the composition is used to achieve a more immediate beneficial effect on the subject, and the composition is administered daily for at least 1 week, 2 weeks, 3 weeks, 1 month, 2 months, 6 months, or 9 months to the subject. In some embodiments, administration is "continuous" or "consecutive" for the length of the treatment period. The term "continuous" or "consecutive" in reference to "administration" means that the frequency of administration is at least once daily. Thus, e.g., the phrase "the composition is administered continuously for more than three weeks" indicates that the composition is administered at least once daily for at least 21 consecutive calendar days. Note, however, that the frequency of administration can be greater than once daily and still be "consecutive," e.g., twice or even three times daily. Additionally, administration of the composition for "consecutive" days can be achieved by dosage forms that administer the composition for longer than a single day. For example, a single transdermal patch that delivers a daily dosage amount of the compound of Formula I produced by the methods of the present invention for 7 consecutive days would be considered to have "administered" the compound for 7 consecutive days.

The terms "treat" and "treatment" refer to both therapeutic treatment and prophylactic or preventative measures, wherein the object is to prevent, inhibit, reverse or slow down (lessen) an undesired physiological condition, disorder or disease, or obtain beneficial or desired chemical results. For purposes of this Invention, beneficial or desired clinical results include, but are not limited to, alleviation of symptoms; diminishment of extent of condition, disorder or disease; stabilized (i.e., not worsening) state of condition, disorder or disease; delay in onset, or slowing, of condition, disorder or disease progression; amelioration of the condition, disorder or disease state, remission (whether partial or total); or enhancement or improvement of condition, disorder or disease. Treatment also includes, but is not limited to, eliciting a cellular response that is clinically significant, without excessive levels of side effects. "Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression can be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Subject" refers to human and non-human animals, e.g., domestic and farm animals, and zoo, sports, and companion animals such as household pets and other domesticated animals such as, but not limited to, cattle, sheep, ferrets, swine, horses, rabbits, goats, dogs, cats and the like. In some embodiments, companion animals are dogs and cats.

The compounds can be useful in treating or suppressing mitochondrial disorders, and methods of using such compounds for modulation of energy biomarkers. "Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and/or enhancement.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. For example, to normalize an energy biomarker in a subject which is depressed in a disease state means to increase the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it can be desirable to increase the level of ATP in that subject to a level above the normal level of ATP in that subject. Enhancement can also be of beneficial effect in a subject suffering from a disease or pathology such as a mitochondrial disease, in that normalizing an energy biomarker cannot achieve the optimum outcome for the subject; in such cases, enhancement of one or more energy biomarkers can be beneficial, for example, higher-than normal levels of ATP, or lower-than-normal levels of lactic acid (lactate) can be beneficial to such a subject.

EXAMPLES 500 mg alpha-tocotrienol were transferred to a 4 mL vial into which 1:3 ethanol:methyl tert-butyl ether (MTBE) (0.48:1.12 mL) was added. To this solution, ferric (III) chloride hexahydrate (1.27 g) in 0.48:0.79 (1:2) ethanol water was added in four portions, each portion providing 1 equivalent of ferric chloride per unit of alpha-tocotrienol, resulting in an overall metal salt oxidizing agent/alpha-tocotrienol ratio of 4:1. The first aliquot was added into the vial and stirred for approximately 30±5 minutes. The mixture was allowed to settle and the aqueous layer was removed to waste. Ferric chloride additions were carried out three more times for a total of four aliquots. After the last aqueous layer was removed to waste, the ethanol:TBME containing the resulting -alpha-tocotrienol quinone was washed with water four times and agitated for 10 minutes. The aqueous layer was removed to waste. The batch was sampled and analyzed by an in-process HPLC method.

The ethanol:MTBE containing alpha-tocotrienol quinone was then washed with deionized water containing 20% (wt/wt) sodium chloride and agitating for a minimum of 5 minutes. The sodium chloride solution was then removed to waste.

The ethanol:TBME containing alpha-tocotrienol quinone was then washed with water containing sodium bicarbonate and agitating for a minimum of 5 minutes. The sodium bicarbonate solution was then removed to waste. The organic layer was charged into a rotary evaporator and the solvent was removed under vacuum at 35° C. The crude product was dissolved in and rinsed out of the evaporation flask with n-heptane.

The Summary and Abstract sections can set forth one or more but not all exemplary embodiments of the present invention as contemplated by the inventor(s), and thus, are not intended to limit the present invention and the appended claims in any way. The breadth and scope of the present invention should not be limited by any of the above-described exemplary embodiments.

All of the various embodiments or options described herein can be combined in any and all variations. The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. If a range is indicated, such as "approximately 50° C. to 60° C.," it is understood that both the values specified by the endpoints are included, and that values close to each endpoint or both endpoints are included for each endpoint or both endpoints; that is, "approximately 50° C. to 60° C." is equivalent to reciting both "50° C. to 60° C." and "approximately 50° C. to approximately 60° C."

All documents cited herein are each entirely incorporated by reference herein.

What is claimed is:

1. A method of producing alpha-tocotrienol quinone of Formula I:

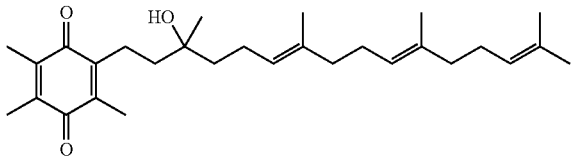

Formula I or a stereoisomer thereof, the method comprising opening of alpha-tocotrienol to alpha-tocotrienol quinone of Formula I in the presence of non-alpha-tocotrienols by oxidizing alpha-tocotrienol with a metal salt oxidizing agent wherein the metal salt oxidizing agent is iron(III) nitrate (Fe(III) $NO_3$), wherein the stoichiometric ratio of metal salt oxidizing agent/alpha-tocotrienol is at least about 4:1 and wherein said metal salt oxidizing agent is optionally added in sequential additions.

2. The method according to claim 1 comprising oxidizing the alpha-tocotrienol with the metal salt oxidizing agent in a biphasic solution, wherein a first solution comprises the alpha-tocotrienol dissolved in a non-polar solvent; a second solution comprises the metal salt oxidizing agent dissolved in a polar solvent; and the separate first and second solutions are mixed to permit the oxidation.

3. The method according to claim 1, wherein the metal salt oxidizing agent is sufficient to oxidize at least about 98% of the alpha-tocotrienol into the alpha-tocotrienol quinone.

4. The method according to claim 3, wherein the composition resulting from the oxidation has less than about 1% of one or more non-alpha-tocotrienol quinone compounds selected from alpha-tocotrienol, beta-tocotrienol, beta-tocotrienol quinone, gamma-tocotrienol, gamma-tocotrienol quinone, delta-tocotrienol, delta-tocotrienol quinone, or combinations thereof.

5. The method according to claim 3, wherein the composition resulting from the oxidation has less than about 0.7% of one or more non-alpha-tocotrienol quinone compounds, selected from alpha-tocotrienol, beta-tocotrienol, beta-tocotrienol quinone, gamma-tocotrienol, gamma-tocotrienol quinone, delta-tocotrienol, delta-tocotrienol quinone, and combinations thereof.

6. The method according to claim 3, wherein the composition resulting from the oxidation has less than about 0.2% of one or more non-alpha-tocotrienol quinone compounds, selected from alpha-tocotrienol, beta-tocotrienol, beta-tocotrienol quinone, gamma-tocotrienol, gamma-tocotrienol quinone, delta-tocotrienol, delta-tocotrienol quinone, and combinations thereof.

7. The method according to claim 2, wherein the non-polar solvent is alcohol, ether, or a mixture of alcohol and ether, and the polar solvent is water or a mixture of water and alcohol.

8. The method according to claim 1, wherein the non-polar solvent is an approximately 1:2 mixture of ethanol and methyl tert-butyl ether (MTBE), and the polar solvent is an approximately 2:1 mixture of water and ethanol.

9. The method according to claim 2, where the metal salt oxidizing agent is serially added in multiple portions, wherein (1) a first portion of the second solution is added to the first solution to react with the alpha-tocotrienol, followed by (2) removal of the polar phase of the first portion, and repeating steps (1) and (2) for the remaining portions of the second solution.

10. The method according to claim 8, where the iron (III) nitrate is serially added in three or four portions, wherein (1) a first portion of iron(III) nitrate is added to the alpha-tocotrienol, followed by (2) removal of the polar phase of the first portion, and repeating steps (1) and (2) for the remaining portions of iron(III) nitrate.

11. The method according to claim 9, where the oxidation reaction is allowed to proceed while measuring the formation of one or more undesired side-products and is interrupted when one or more of the undesired side-products are detected.

12. The method according to claim 11, where the oxidation reaction is allowed to proceed while the formation of the one or more undesired side-products is measured and the oxidation is interrupted when the level of a single side-product is about 1%.

13. The method according to claim 11, where the oxidation reaction is allowed to proceed while the formation of the one or more undesired side-products is measured and the oxidation is interrupted when the level of a single side-product is about 0.5%.

14. The method of claim 1, where the metal salt oxidizing agent is not added in sequential additions.

* * * * *